United States Patent
Hong (10) Patent No.: US 9,012,370 B2
(45) Date of Patent: Apr. 21, 2015

(54) METHOD FOR MEASURING CHROMOSOME, GENE OR SPECIFIC NUCLEOTIDE SEQUENCE COPY NUMBERS USING SNP ARRAY

(75) Inventor: Kyeong Man Hong, Gyeonggi-do (KR)

(73) Assignee: National Cancer Center, Gyeonggi-do (KR)

(*) Notice: Subject to any disclaimer, the term of this patent is extended or adjusted under 35 U.S.C. 154(b) by 1049 days.

(21) Appl. No.: 12/810,229

(22) PCT Filed: Mar. 5, 2009

(86) PCT No.: PCT/KR2009/001111
§ 371 (c)(1),
(2), (4) Date: Dec. 15, 2010

(87) PCT Pub. No.: WO2009/113779
PCT Pub. Date: Sep. 17, 2009

(65) Prior Publication Data
US 2011/0105352 A1    May 5, 2011

(30) Foreign Application Priority Data
Mar. 11, 2008  (KR) .................. 10-2008-0022500

(51) Int. Cl.
C40B 30/04    (2006.01)
C12Q 1/68    (2006.01)
(52) U.S. Cl.
CPC .............. C12Q 1/6827 (2013.01); C40B 30/04 (2013.01); *C12Q 2600/158* (2013.01)
(58) Field of Classification Search
None
See application file for complete search history.

(56) References Cited

U.S. PATENT DOCUMENTS

| | | |
|---|---|---|
| 5,143,854 A | 9/1992 | Pirrung et al. |
| 5,578,832 A | 11/1996 | Trulson et al. |
| 5,593,839 A | 1/1997 | Hubbell et al. |
| 5,631,734 A | 5/1997 | Stern et al. |
| 5,733,729 A | 3/1998 | Lipshutz et al. |
| 5,795,716 A | 8/1998 | Chee |
| 5,834,758 A | 11/1998 | Trulson et al. |
| 5,936,324 A | 8/1999 | Montagu |
| 5,974,164 A | 10/1999 | Chee |
| 5,981,956 A | 11/1999 | Stern |
| 6,025,601 A | 2/2000 | Trulson et al. |

(Continued)

FOREIGN PATENT DOCUMENTS

| KR | WO 2006/011738 A1 * | 2/2006 | ............... C12Q 1/68 |
|---|---|---|---|
| WO | 99/47964 A1 | 9/1999 | |

(Continued)

OTHER PUBLICATIONS

Kukita et al. (2005) Genome Research vol. 15 pp. 1511 to 1518.*

(Continued)

*Primary Examiner* — Chistian Boesen
(74) *Attorney, Agent, or Firm* — Lathrop & Gage LLP; Andrew T. Wilkins; Brian C. Trinque (57) ABSTRACT

The present invention relates to a method for measuring the copy number of a chromosome, gene or specific nucleotide sequence, comprising the steps of: (a) mixing a homozygous DNA with a test sample DNA; (b) analyzing the DNA mixture by means of SNP array; and (c) determining the copy number of a chromosome, gene, or specific nucleotide sequence by measuring the difference in signal output from the homozygous DNA and the test sample DNA.

4 Claims, 8 Drawing Sheets

(56) References Cited

U.S. PATENT DOCUMENTS

| | | | |
|---|---|---|---|
| 6,066,454 | A | 5/2000 | Lipshutz et al. |
| 6,090,555 | A | 7/2000 | Fiekowsky et al. |
| 6,141,096 | A | 10/2000 | Stern et al. |
| 6,185,030 | B1 | 2/2001 | Overbeck |
| 6,185,561 | B1 | 2/2001 | Balaban et al. |
| 6,188,783 | B1 | 2/2001 | Balaban et al. |
| 6,201,639 | B1 | 3/2001 | Overbeck |
| 6,218,803 | B1 | 4/2001 | Montagu et al. |
| 6,223,127 | B1 | 4/2001 | Berno |
| 6,225,625 | B1 | 5/2001 | Pirrung et al. |
| 6,229,911 | B1 | 5/2001 | Balaban et al. |
| 6,308,170 | B1 | 10/2001 | Balaban |
| 2003/0143554 | A1 | 7/2003 | Berres et al. |
| 2006/0134674 | A1 | 6/2006 | Huang et al. |

FOREIGN PATENT DOCUMENTS

| | | |
|---|---|---|
| WO | WO 2007/048469 | 5/2007 |
| WO | WO 2007/068305 | 6/2007 |

OTHER PUBLICATIONS

Hoyer, Juliane et al., "Molecular karyotyping in patients with mental retardation using 100K single-nucleotide polymorphism arrays," J. Med. Genet., vol. 44:629-636 (2007).

Komura, Daisuke et al., "Genome-wide detection of human copy number variations using high-density DNA oligonucleotide arrays," Genome Research, vol. 16:1575-1584 (2006).

Lindblad-Toh, Kerstin et al., "Loss-of-heterozygosity analysis of small-cell lung carcinomas using single-nucleotide polymorphism arrays," Nature Biotechnology, vol. 18:1001-1005 (2000).

Pont-Kingdon, Genevieve et al., "Rapid Detection of Aneuploidy (Trisomy 21) by Allele Quantification Combined with Melting Curves Analysis of Single-Nucleotide Polymorphism Loci," Clinical Chemistry, vol. 49(7):1087-1094 (2003).

Rigaill, Guillem et al., "ITALICS: an algorithm for normalization and DNA copy number calling for Affymetrix SNP arrays," Bioinformatics, vol. 24(6):768-774 (2008).

Lee, et al: Rapid Detection of Trisomy 21 by Homologous Gene Quantitative PCR (HGQ-PCR); Hum Genet; 1997, vol. 99, pp. 364-367.

* cited by examiner

Sample genomic DNA  Parthenogenetic cell line genomic DNA

Mix

SNP analysis

: when alter homozygous alleles are only analyzed, signals from two types of DNAs are different from each other.
Thus, relative signal intensity can be defined as follow.

$$\text{signal ratio (SR)} = \frac{\text{SNP signal of sample}}{\text{SNP signal of parthenogenetic cell line}}$$

: Analysis on the region having the different SR from that of other regions

METHOD FOR MEASURING CHROMOSOME, GENE OR SPECIFIC NUCLEOTIDE SEQUENCE COPY NUMBERS USING SNP ARRAY

RELATED APPLICATIONS

This application is a 35 U.S.C. §371 national stage filing of PCT Application No. PCT/KR2009/001111 filed on Mar. 5, 2009, which claims priority to, and the benefit of, Korean Application No. 10-2008-0022500 filed on Mar. 11, 2008. The contents of the aforementioned applications are hereby incorporated by reference.

BACKGROUND OF THE INVENTION

1. Field of the Invention

The present invention relates to a method for measuring the copy number of a chromosome, gene or specific nucleotide sequence, comprising the steps of: (a) mixing a homozygous DNA with a test sample DNA; (b) analyzing the DNA mixture by means of SNP array; and (c) determining the copy number of a chromosome, gene, or specific nucleotide sequence by measuring the difference in signal output from the homozygous DNA and the test sample DNA.

2. Description of the Related Art

Changes in specific chromosomal sequences are frequently implicated in human diseases and syndromes. Such changes include the addition or the deletion of one entire chromosome as in Down's syndrome, deletions of several million base pairs as in DiGeorge syndrome, and deletions or duplications of small chromosomal fragments as in Becker or Duchenne muscular dystrophy. A subtelomeric deletion is also frequently reported in mental retardation patients (Lamb et al., 1989). In addition, chromosomal regions of specific genes such as BRCA1 or MLH1/MLH2 are commonly changed in tumors, which is known to be important for gene expressions (Petrij-Bosch et al., 1997; Wijnen et al., 1998). An analysis of the copy number change of genes can be important for the treatment of cancer patients, as can be seen from the example of using ERBB2-specific antibodies to treat a breast cancer patient having ERBB2 gene amplified (Leyland-Jones and Smith, 2001).

At present, many techniques are used to determine the copy number of chromosomal changes. The most standardized method of measuring the number and structural changes of chromosomes is a karyotyping method. According to this method, it is required to culture the patient's blood, fibroblast or amniotic cells, and much time and manpower are necessary to interpret the result thereof. The karyotyping method usually can detect 1 mega base or more of the chromosomal changes only. This sensitivity issue can be made up for with a fluorescent in situ hybridization (FISH) method. However, the FISH method also requires much time and manpower and does not usually measure the changes of four or more different target genes at a time (Klinger et al., 1992). In addition, a multicolor chromosome painting method is introduced as a method for automatization of the karyotyping. The method allows the deletion, duplication or translocation of the chromosome to be easily detected by labeling portions of each chromosome with fluorescent materials of different colors (U.S. Pat. No. 6,066,459). Although the multicolor chromosome painting method increases the sensitivity somewhat, compared to the karyotyping method, it basically needs a cell culture and a post-process which are required for the karyotyping.

In order to overcome the requirements of time and manpower, several molecular methods have been recently developed to detect the chromosomal changes. Array based-comparative genomic hybridization (CGH) is one of the most promising methods and many trials have been attempted for application to the diagnosis on genetic diseases or the detection of chromosomal changes in cancer tissues (Pinkel et al, 1998; U.S. Pat. Nos. 6,197,501 and 6,159,685). This method immobilizes BAC clones on a substrate surface to form an array, and pre-labeled standard DNA and sample DNA are hybridized to the array. According to the method, a relative amount of signals from the standard and sample DNAs is compared to detect the chromosomal changes such as deletion or duplication.

In addition, there is a method of determining the copy number by measuring the relative amplification with multiplex PCR method (Rahil et al., 2002). As a modified method thereof, a multiplex ligation-dependent probe amplification (MLPA) was recently introduced (Schouten et al., 2002; Patent number WO9615271).

Loss of heterozygosity (LOH) is the most common method to detect deletion or duplication of a chromosome. For research of LOH, microsatellite markers (Call et al., 1990) have been used. However, the LOH method using microsatellite markers cannot distinguish whether a chromosomal change is deletion or duplication, except for in the case of homozygous deletion.

Pont-Kindon and Lyon (2003) reported another method of using SNP to detect a chromosomal abnormality. They used a melting curve analysis to detect the relative amount of heterozygous alleles. The method detects that there is a trisomy when the relative amount of two alleles is different from a normal ratio.

In addition, there was introduced a method of detecting deletion or duplication of chromosome by means of SNP array (Lindblad-Toh et al., 2000). The method has enormous potential that the array can be extended to detect a large number of SNPs. However, the SNP array for the detection of chromosomal changes has the limitation that it requires the presence of heterozygous alleles in the test DNA. Common SNPs are those that are present in more than 5% of the population, but the number of SNPs and heterozygote frequency used for CNV (copy number variation) are low in a single gene. Therefore, there is an urgent need for improvement of the method in order to detect specific SNPs of interest.

Therefore, the present inventors have made an effort to solve the above problems and to develop more effective methods for measuring the copy number of a chromosome, gene or specific nucleotide sequence. Finally, the present inventors developed a method comprising the steps of mixing a homozygous DNA with a test sample DNA and analyzing the DNA mixture by means of SNP array capable of measuring rare SNP to measure the difference in signal output from each sample. They found that the method is able to allow more accurate values to be obtained compared to the other molecular methods of determining the copy number of a specific gene as well as remarkably reduce costs and required manpower, thereby completing the present invention.

SUMMARY OF THE INVENTION

It is an object of the present invention to provide a method for measuring the copy number of a chromosome, gene or specific nucleotide sequence, comprising the steps of: (a) mixing a homozygous DNA with a test sample DNA; (b) analyzing the DNA mixture by means of SNP array; and (c)

determining the copy number of a chromosome, gene, or specific nucleotide sequence by measuring the difference in signal output from the homozygous DNA and the test sample DNA.

Effects of the Invention

According to the analysis kit and method for measuring the copy number of a chromosome, gene or specific nucleotide sequence of the present invention, it is possible to obtain a more accurate value than in the other molecular methods when determining the copy number of specific genes as well as to remarkably reduce the time and necessary manpower, when analyzing the change of the chromosome. Therefore, the method can readily detect duplications and deletions of a chromosome or gene, compared to the known methods.

DESCRIPTION OF THE PREFERRED EMBODIMENTS

In one aspect, in order to achieve the above object, the present invention relates to a method for measuring the copy number of a chromosome, gene or specific nucleotide sequence, comprising the steps of: (a) mixing a homozygous DNA with a test sample DNA; (b) analyzing the DNA mixture by means of SNP array; and (c) determining the copy number of a chromosome, gene, or specific nucleotide sequence by measuring the difference in signal output from the homozygous DNA and the test sample DNA.

Specifically, the homozygous DNA in step (a) is any cell line without limitation, as long as it is homozygous, and in accordance with the purpose of the present invention, preferably a homozygote derived from a parthenogenetic or hydatidiform mole cell line.

As used herein, the term "parthenogenetic cell line" refers to a diploid (2n) cell line developed from an unfertilized egg (n), and the term "hydatidiform mole cell line" refers to a cell line from a mass of abnormal embryonic tissue, of which DNA (2n) is derived from a sperm (n) only. Therefore, all DNAs of parthenogenetic and hydatidiform mole cell lines are homozygous DNAs.

As used herein, the term "homozygote" may be a haplotype or BAC clone DNA, in addition to the above described parthenogenetic or hydatidiform mole cell line. The DNA mixture is amplified, and then used in the next step, SNP array.

As used herein, the term "amplification" refers to a process by which a target sequence is further synthesized. The amplification process can be performed by a conventional method used in the art without limitation, preferably polymerase chain reaction (PCR). This process is performed to obtain sufficient DNA from the sample. In general, the amplification process includes processes of annealing, synthesis (extension or elongation), and denaturation. The sample sequences are amplified by the above-mentioned procedure, and then used in the SNP array.

As used herein, the term "sample" is a biological substance from a living organism and mainly means a biological substance originating from a human. The term "test sample" refers to a subject for which the copy number of the chromosome, gene or specific nucleotide sequence is measured. The type of sample to be used as the test sample is not particularly limited, and it may be preferably a sample that is obtained from an individual suspected of having an abnormality or change in the number of chromosomes. In the preferred Example of the present invention, a sample from a Down's syndrome subject was used as a test sample, and changes in the copy number of genes were analyzed.

Step (b) is a step of fragmentation and labeling of the amplified DNA, and hybridization of the labeled DNA on a SNP array chip. At this time, it is preferable that different types of fluorescent materials are used depending on the type of base incorporated in the SNP position. When the mixture of homozygous DNA and sample DNA is analyzed by SNP array, a signal ratio can be obtained by alleles from two different types of cells or two different bases when the bases are different from each other. If chromosomal abnormality such as deletion or duplication occurs, the signal ratio becomes different from that of normal chromosome. In the present invention, the SNP array can be performed by the SNP array methods typically used in the art, and commercially available SNP array chips, for example, SNP array chips (10K, 100K, 500K etc.) manufactured by Affymetrix.

As used herein, the term "single nucleotide polymorphism" (SNP) is a polymorphism of a single nucleotide. That is, a single nucleotide in the genome differs between members of paired chromosomes within a population, and SNPs typically occur about once every 300-1000 base pairs. Thus, three million SNPs exist in the human genome.

SNPs are classified into rSNP (regulatory SNP) that is found in the region involved in regulation of transcriptional activity such as the promoter region, cSNP (coding SNP) that induces amino acid mutations in exons, iSNP (intronic SNP) found in introns, sSNP (silent SNP) that induces silence mutations in exons, and gSNP (genome SNP) found in other genomic regions, and the type of SNP applicable to the present invention is not limited to these examples.

In human genomes, 99.9% of the DNA sequence is identical, and the remaining 0.1% of DNA contains sequence variations which are associated with diversity in the population, such as susceptibility to diseases and individual response to medicine. Recently, it has been suggested that SNPs are directly associated with the susceptibility to, or side effect of drugs. Since SNPs are highly abundant, and distributed throughout the genome, they are reliable polymorphisms that can be used to study susceptibility to diseases or individual response to medicine. By studying SNPs, the relationship between natural genetic variations and diseases can be understood, and drug susceptibility or side effects can be also analyzed. Therefore, these SNP studies may provide a starting point for further screening of genetic diseases and the design of personalized drug treatments.

In general, SNPs are defined by very highly conserved surrounding sequences. The replacement of one single nucleotide with any one of the other nucleotides or deletion or duplication of nucleotide results in a SNP. In particular, rare SNP refers to a SNP with allele frequency less than 5%, and common SNP refers to a SNP with allele frequency more than 5%. The rare SNP may occur differently depending on race or ethnicity. In accordance with the purpose of the present invention, the definition of rare SNP may vary, depending on whether the defined population is confined to the human race or confined to a specific population. Also, it is apparent that even though a variation is present as common SNP in one population, it can be a rare SNP in other populations. Therefore, even though a rare SNP is only present in a certain population, it is regarded as rare SNP in the present invention. As described above, rare SNPs that occur differently depending on race or ethnicity can be used to constitute effective arrays. Based on the specificity of the population to be analyzed, the population scale may be determined. Thus, it is apparent that the definition of rare SNP may vary. Such SNP profiles are useful in screening disease models of a specific population, as well as the human race.

As used herein, the term "polymorphic site" refers to a locus at which diverse bases can be found. Usually, SNP has at least two alleles, and a frequency thereof refers to an occurrence of 1% or more in the general public. A form of the allele occurring most frequently is referred to as a wild-type form, and a form of the allele occurring less frequently is referred to as a mutant allele.

As used herein, the term "allele" refers to different versions of the same gene present in a given locus on homologous chromosomes. An allele may be used to indicate one form of a polymorphism, for example, the majority of SNPs are biallelic.

As used herein, the term "SNP array chip" refers to a biological microchip capable of analyzing the presence of SNPs contained in the sample DNA by arranging and attaching several hundred to several hundred thousand biomolecules as a probe, such as DNA, DNA fragment, cDNA, oligonucleotide, RNA or RNA fragment having the known sequences, which are immobilized at intervals on a small solid substrate formed of glass, silicon or nylon. Hybridization occurs between nucleic acids contained in the sample and probes immobilized on the surface, depending on the degree of complementarity. By detecting and interpreting the hybridization, information on the materials contained in the sample can be concurrently obtained.

Step (c) is a step of determining the copy number of a chromosome, gene, or specific nucleotide sequence by measuring the difference in signal output from the homozygous DNA and the test sample DNA.

The signal detection may be performed by any typical method used in the art without limitation, for example, a laser-induced fluorescence detecting method, an electrochemical detecting method, a mass detecting method or Surface Plasmon Resonance (SPR). In the laser-induced fluorescence detecting method, a fluorescent material is coupled with a sample DNA, and after hybridization, the result of the reaction is detected using a fluorescence detecting apparatus to optically determine the hybridization. In the electrochemical detecting method, hybridization is detected by using an electrochemical reaction, that is, a reduction and oxidation reaction of other chemical materials on an electrode. In the mass detecting method, an interaction between a probe and a sample DNA is electrically signalized and detected. As a typical example, there is an electrochemical Quartz Crystal Microbalance (QCM) detecting method for measuring a frequency variation depending on a mass of the capturing probe immobilized on quartz, which vibrates at a high frequency. Surface Plasmon Resonance (SPR) is a phenomenon which induces signal changes upon binding biomolecules such as proteins to the surface of a sensor, and detects an SPR signal change generated by a mass change of probes by optical methods such as quantized oscillations of free electrons propagating along the metal's surface. This method is able to detect the DNA binding affinity due to mass difference without labeling the sample with additional fluorescent materials. A preferred method may be the laser-induced fluorescence detecting method.

The copy number of a chromosome, gene, or specific nucleotide sequence can be easily determined by measuring the difference in signal output from the homozygous DNA and the test sample DNA. It is possible to determine both the increased copy number and decreased copy number by the method of determining the copy number of the present invention. That is, increased copy number due to chromosomal duplication (e.g., trisomy or tetrasomy in autosome) and decreased copy number due to chromosomal deletion can be determined.

Specifically, in the case of an alter homozygous allele, namely, when the SNP allele of the test sample DNA is homozygous but its base sequence is different from that of the allele of homozygous cell line DNA, the SNP alleles of the test sample and homozygous cell line are different from each other. Thus, the ratio of SNP signals (SR) from each DNA is measured, thereby analyzing changes in the copy number.

Formula:
SNP Signal of Sample/SNP Signal of Homozygous Cell Line

For example, when a 1:1 mixture of the sample DNA and homozygous cell line DNA is used in the SNP array, the ratio of SNP signals (SR) from each DNA will be 1:1. In this regard, if the ratio is not 1:1, it indicates changes in the copy number. If it is difficult to keep the mixing ratio at 1:1 during practical procedures, the ratio of total signals from two DNAs are measured to correct SR, thereby more accurately measuring the changes in copy number.

In addition, when the test sample DNA is a heterozygous allele, the signal intensity from two types of bases appears at a ratio of 1:3 or 3:1 by the method of the present invention. The ratio will vary depending on the changes in copy number. Thus, even though the test sample DNA is a heterozygous allele, the copy number can be determined.

Figure 5:
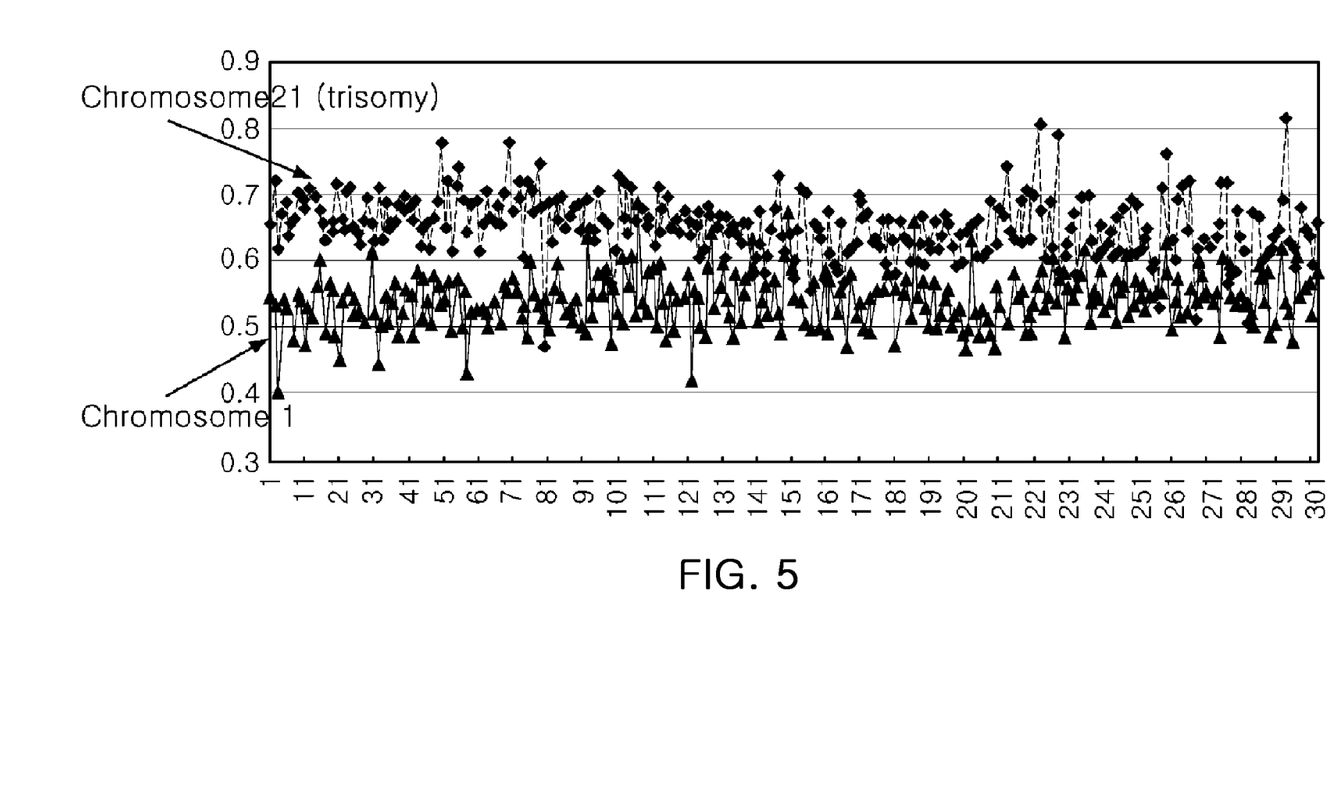
FIG. 5 is a diagram showing the result of Illumina SNP array (317K Duo) for copy number analysis by using a Down's syndrome sample (test sample) and normal control DNA (homozygote), in which triangles represent the result of SNP analysis on chromosome 1 and diamonds represent the result of SNP analysis on chromosome 21.
Figure 6:
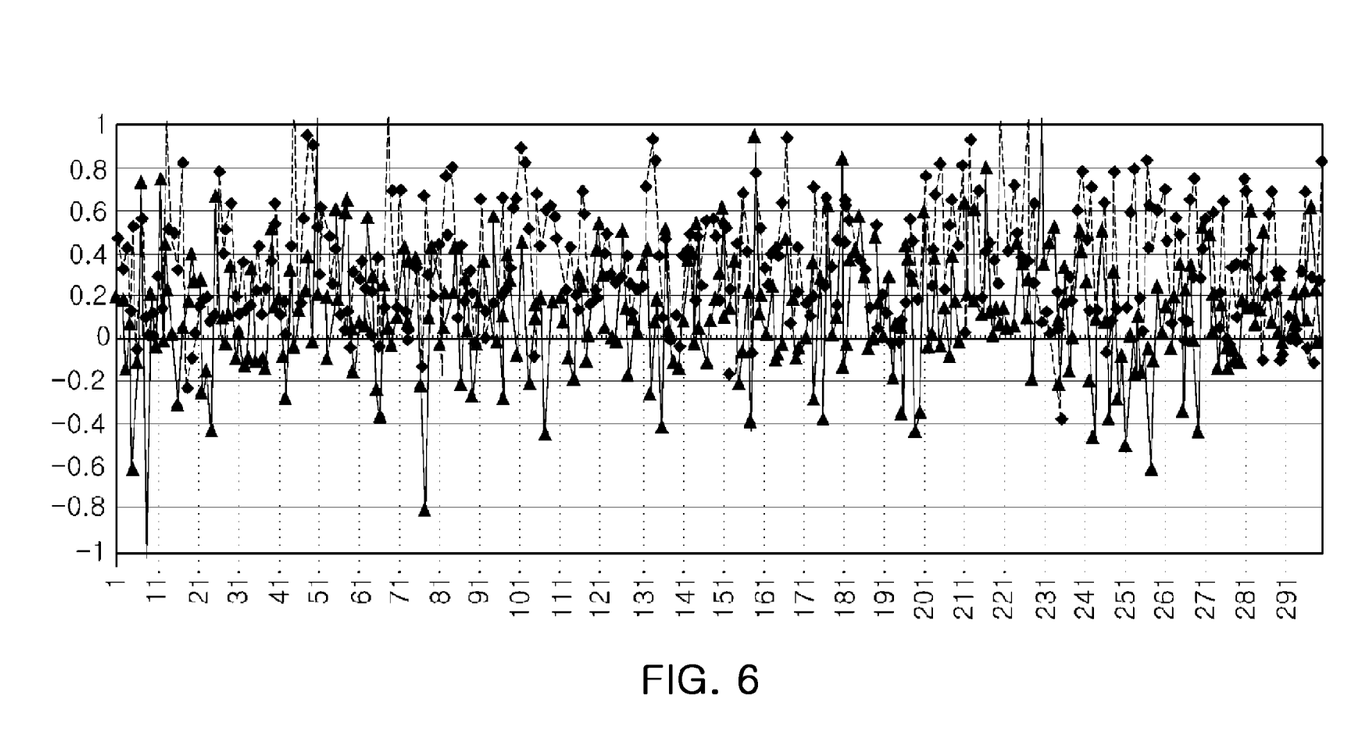
FIG. 6 is a diagram showing the result of signal intensity comparison after Illumina SNP array (317K Duo) analysis using Down's syndrome DNA (chromosome 1 and chromosome 21) as a sample, in which triangles represent the result of SNP analysis on chromosome 1 and diamonds represent the result of SNP analysis on chromosome 21.
Figure 7:
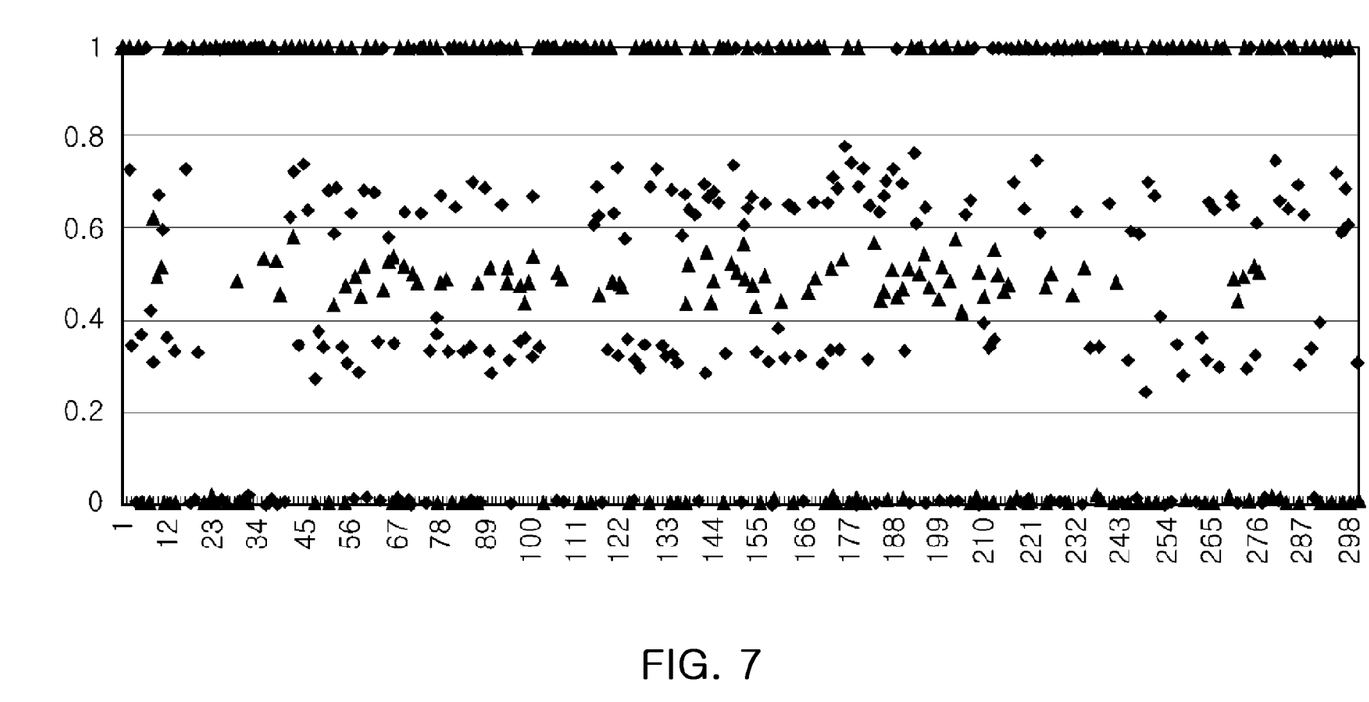
FIG. 7 is a diagram showing the signal ratio of each SNP after Illumina SNP array (317K Duo) analysis using Down's syndrome DNA (chromosome 1 and chromosome 21) as a sample, in which triangles represent the result of SNP analysis on chromosome 1 and diamonds represent the result of SNP analysis on chromosome 21.

As compared to the known methods of analyzing normal DNAs singly, the method of the present invention is able to provide more valuable information on changes in the copy number. In accordance with one preferred embodiment of the present invention, even though using a much smaller number of SNPs, chromosomal duplications and deletions of specific materials can be more easily and accurately detected by the method of the present invention (FIG. 5), as compared to the known analysis method using the test sample only (FIGS. 6 and 7).

As used herein, the term "alter homozygous allele" refers to SNP where the SNP allele of the test sample DNA is homozygous but its base sequence is different from that of the allele of the homozygous cell line DNA, and the term is introduced by the present inventors for better description.

In the preferred embodiment, when the method of the present invention is applied to SNP array for rare SNPs, information on the copy number changes can be more usefully obtained.

Figure 1:
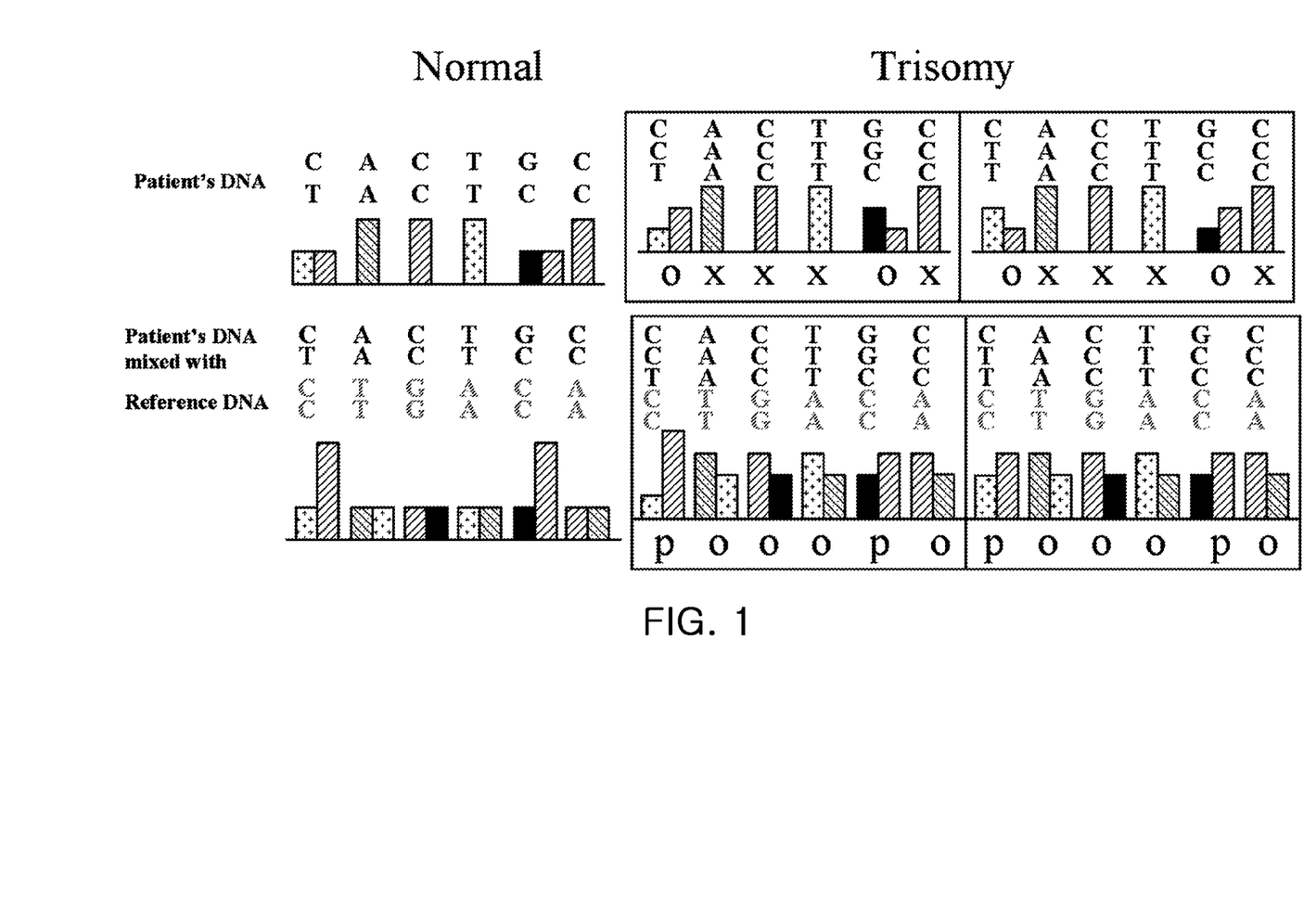
FIG. 1 is a diagram showing the relative signal intensity of each allele, when a normal test sample DNA is singly analyzed and a 1:1 mixture of normal test sample DNA and homozygous DNA is analyzed.
Figure 2:
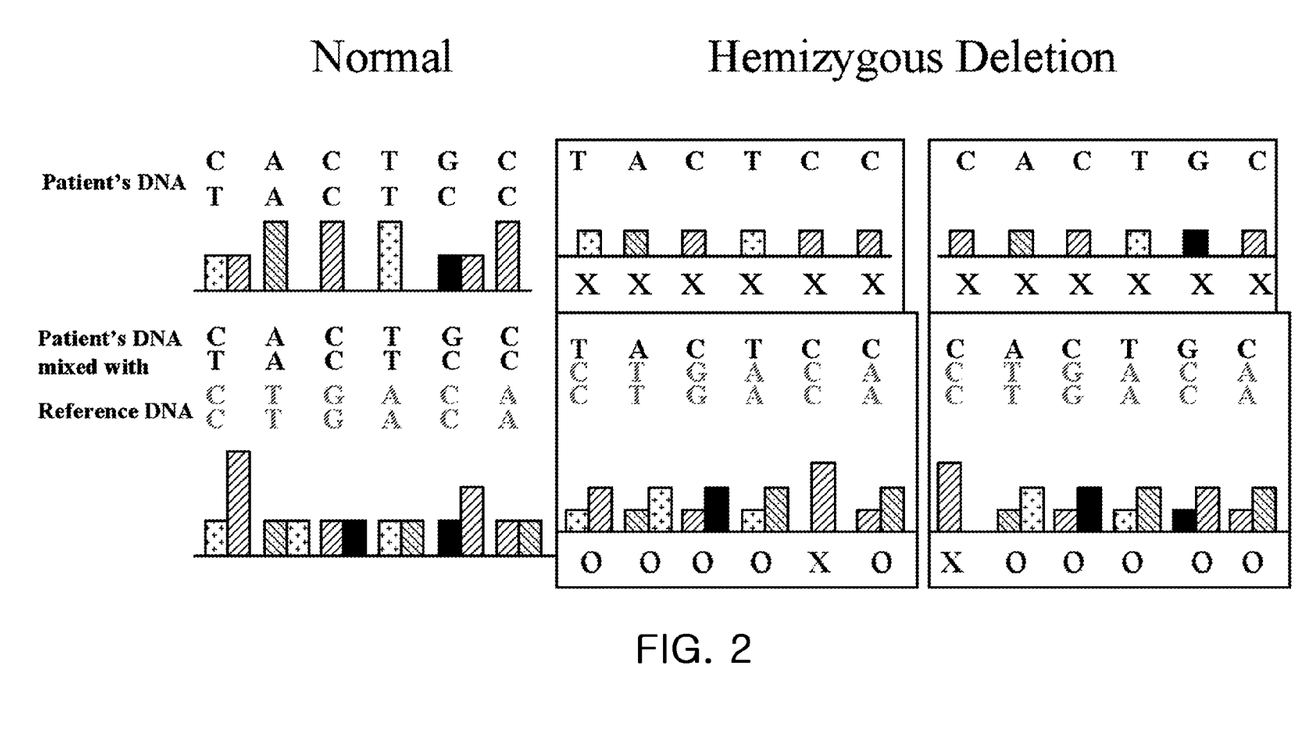
FIG. 2 is a diagram showing the relative signal intensity of each allele, when deletion of one allele occurs.
Figure 3:
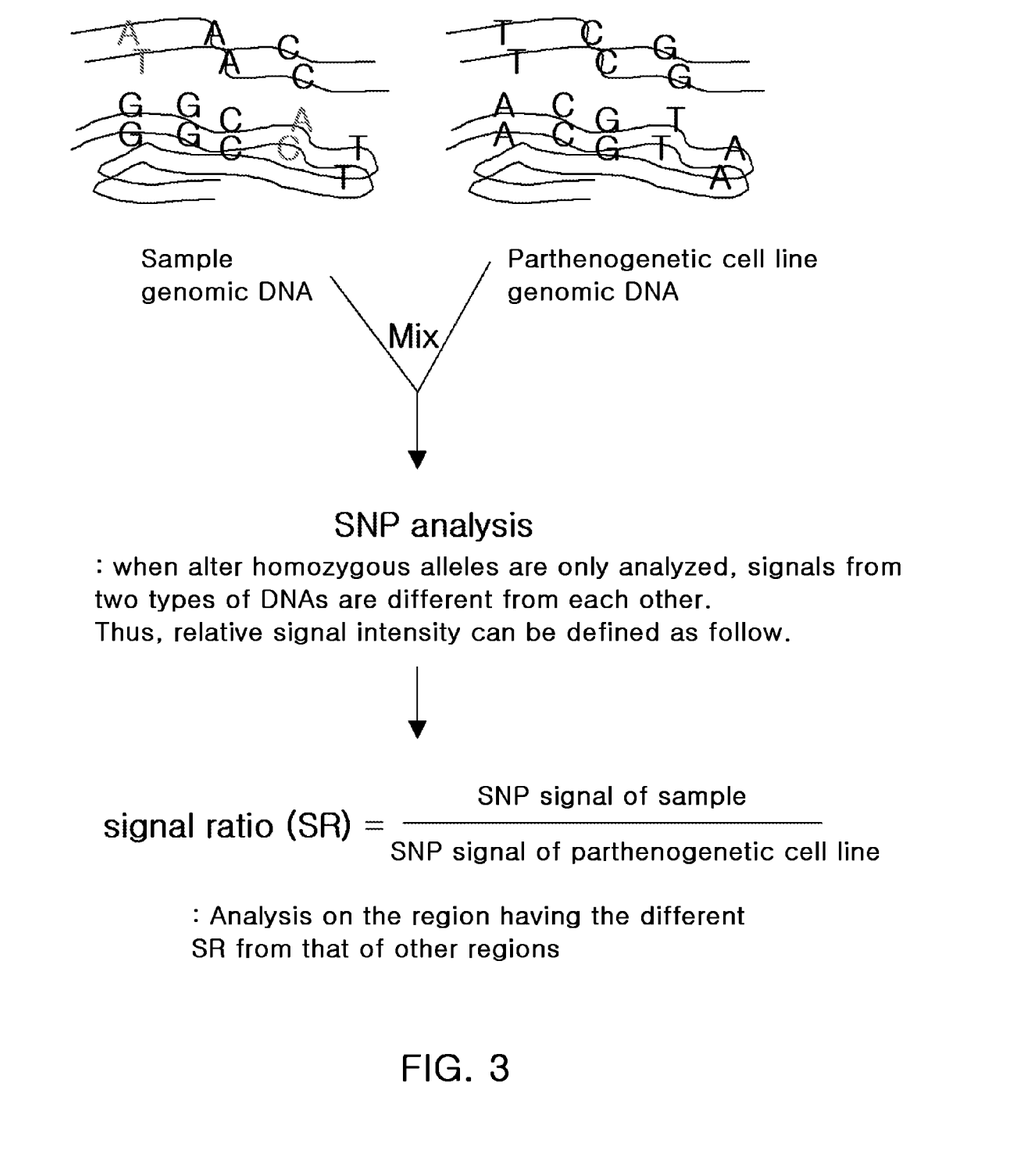
FIG. 3 is a diagram illustrating the experimental procedure and analysis method of the present invention.

For example, as shown in FIGS. 1 and 2, upon analyzing a normal DNA sample singly, two of six SNPs can be only used in the SNP array. However, when among rare SNPs, SNPs found in homozygous cell line DNA are only selected to be used in the SNP array, much information can be obtained even though using a small number of SNPs. That is, when a SNP array composed of SNPs with a frequency of 5% is used to analyze 100 SNPs, approximately 10 heterozygous SNPs are found, whereby information on the copy number changes can be obtained. Meanwhile, when a SNP array composed of rare SNPs with a frequency less than 1% is used to analyze 100 SNPs, heterozygous alleles more than 98% in the array can be advantageously used. In addition, all SNPs with low frequency can be used. Thus, among parthenogenetic cell lines, cell lines with many rare SNPs are selected or homozygous cell lines of other races are used to more precisely determine changes in the copy number of specific regions.

As such, the method of the present invention is very useful for SNP array composed of rare SNPs only, but also applicable to commercially available SNP arrays composed of both rare and common SNPs. That is, alter homozygous alleles are separately analyzed using commercially available SNP arrays to determine the copy number.

The practice of the present invention may employ conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Biochemistry (Stryer, L. Freeman, New York), Oligonucleotide Synthesis: A Practical Approach (Gait, 1984, IRL Press, London) Lehninger Principles of Biochemistry (Nelson and Cox, 2000, W. H. Freeman Pub., New York) and Biochemistry (Berg et al. 2002, W. H. Freeman Pub., New York), all of which are herein incorporated in their entirety by reference for all purposes.

Methods and techniques applicable to polymer array synthesis in the present invention have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, and WO 99/36760 and WO 01/58593, which are all incorporated herein by reference in their entirety for all purposes.

Nucleic acid arrays are described in many patents including U.S. Pat. Nos. 5,412,087, 6,147,205, 6,262,216, 6,310,189, 5,889,165, and 5,959,098, but the same techniques are applied to polypeptide arrays.

The present invention may also contemplate gene expression monitoring, profiling, library screening, and genotyping techniques. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 10/442,021, 10/013,598, and U.S. Pat. Nos. 5,856,092, 6,300,063, 5,858,659, 6,284,460, 6,361,947, 6,368,799 and 6,333,179.

In the present invention, the genomic sample may be amplified by a variety of mechanisms, some of which may employ PCR. See, for example, PCR Technology: Principles and Applications for DNA Amplification (Ed. H. A. Erlich, Freeman Press, NY, N.Y., 1992); PCR Protocols: A Guide to Methods and Applications (Eds. Innis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202, 4,683,195, 4,800,159, 4,965,188, and 5,333,675.

Hybridization assay procedures are described in: Maniatis et al. Molecular Cloning: A Laboratory Manual ($2^{nd}$ Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davism, P.N.A.S, 80: 1194 (1983).

Methods for signal detection of hybridization are described in U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, and WO99/47964.

The practice of the present invention may also employ conventional biology methods, software and systems. Computer software products of the present invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in Introduction to Computational Biology Methods (PWS Publishing Company, Boston, 1997); Computational Methods in Molecular Biology, (Elsevier, Amsterdam, 1998); Bioinformatics Basics Application in Biological Science and Medicine (CRC Press, London, 2000) and Bioinformatics: A Practical Guide for Analysis of Gene and Proteins (Wiley & Sons, Inc., 2.sup.nd ed., 2001).

The present invention may also make use of various computer program products and software for a variety of purposes, such as probe design, management of data, analysis and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

The present invention can be used to diagnose and to screen chromosome abnormality due to the duplication and deletion, such as trisomy, monosomy and sex chromosome abnormality. In addition, the present invention is useful for the diagnosis of genetic diseases due to the deletion of a small chromosome such as Duchenne muscular dystrophy and for the detection of the small chromosomal changes in diseases having inherited tendency induced by diverse causes, such as mental retardation, Alzheimer's disease and diabetes. Further, the present invention can be used to analyze a change of the copy number of oncogenes and tumor suppressor genes in tumor tissues, or an abnormality of the general chromosome number. The chromosomal copy number differs from individual to individual, and there is a report that such copy number variation is associated with some diseases (Iafrate et al., 2004). Therefore, the present invention can be used for the detection of copy number variation between individuals. In particular, as compared to the known methods, the analysis method of the present invention is a powerful tool to allow the detection of higher multiplication than 3n and effective analysis of amplification of small chromosomal regions.

Hereinafter, the present invention will be described in more detail with reference to the following Examples. However, these Examples are for the illustrative purpose only, and the invention is not intended to be limited by Examples.

EXAMPLE 1

SNP Array for Detection of Increased Copy Number

After a normal test sample DNA was analyzed singly and a 1:1 mixture of normal test sample DNA and homozygous DNA was analyzed, the relative signal intensity of each allele was shown. The relative signal intensity of the allele in the normal test sample (Normal) was shown in the left of the FIGURE. The relative signal intensity of the allele, when the copy number was changed to trisomy, was shown in the right of the FIGURE, where the change in each DNA strand is depicted separately. After analyzing the information on all alleles of the test sample and homozygous DNAs, each allele was analyzed using SNP arrays according to the method of the present invention. When the copy number is measurable, it is represented by ○. When the copy number is not measurable, it is represented by x. p represents that increase or decrease in the copy number cannot be determined by the relative signal intensity of a specific allele but changes are found, and the increase or decrease can be determined by the intensity of total signals.

EXAMPLE 2

SNP Array for Detection of Decreased Copy Number

Deletion of one allele was shown as the relative signal intensity of each allele, where the deletion in each DNA strand is depicted separately. When the SNP array was performed on the test sample only, the deletion could not be determined from the result of one allele, and the possibility of deletion could be determined by analysis of neighboring alleles. However, when the method of the present invention is used, each allele can be analyzed, thereby determining the deletion, and its analytical performance is much improved, compared to the prior methods (FIG. 2).

EXAMPLE 3

Figure 4:
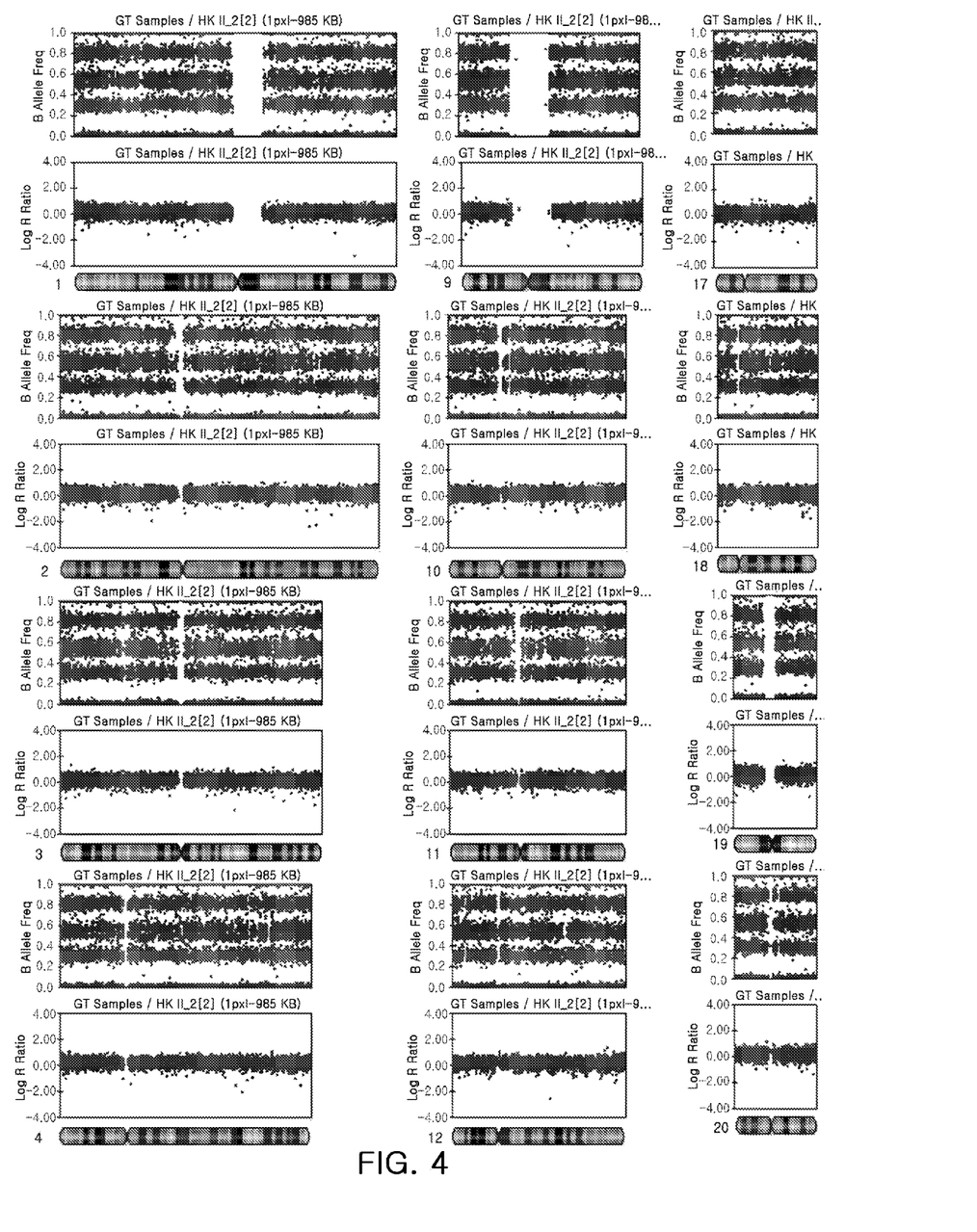
FIG. 4 is a diagram showing the result of SNP array for copy number analysis by using a 1:1 mixture of DNAs from homozygous hydatidiform mole cell line and Down's syndrome cell.

SNP array of homozygous hydatidiform mole DNA and Down's syndrome patient DNAs from homozygous hydatidiform mole cell line and Down's syndrome patient having three copies of chromosome 21 were mixed with each other in a ratio of 1:1, and then the SNP array was used to analyze the copy number. Excluding chromosome 21 and X chromosome, SR was found to be 1:1, 1:3, and 3:1. The chromosome 21 was found to show SR of 2:3, 3:2, 1:4, and 4:1, in which SR of 2:3 or 3:2 indicates three copies of chromosome 21 in Down's syndrome patient (FIG. 4).

EXAMPLE 4

Illumina SNP array of Down's syndrome and normal control DNAs Down's syndrome and normal control DNAs were used as samples, and mixed with the hydatidiform mole DNA (1:1), respectively. Then, Illumina SNP array (317K Duo) was used to perform SNP analysis. Only SNPs showing AA in hydatidiform mole and BB in Down's syndrome cell were analyzed independently. 300 corresponding SNPs were extracted from chromosome 1 and 21, respectively and analyzed (FIG. 5). As a result, it was found that extra chromosome 21 (3n) in Down's syndrome was easily discriminated from normal chromosome 1 (2n) in terms of the copy number.

In order to confirm the usefulness of the detection method of the present invention, Down's syndrome DNA (normal chromosome 1 and three copies of chromosome 21, free of homozygous control DNA) was used as a sample to perform SNP analysis by means of Illumina SNP array (317 DUO). The analysis was typically performed by a signal intensity comparison method and by a method of analyzing the signal intensity ratio of A and B alleles. As in the method of the present invention, 300 SNP results were extracted, and then each result was shown in a graph (FIGS. 6 and 7).

As a result, when the method of the present invention was used (FIG. 5), chromosome or gene amplification can be more easily discriminated, as compared to the method of analyzing only signal intensity without mixing with the normal control sample (FIG. 6). In particular, when the test sample was only used to analyze the signal intensity, the signal intensity of chromosome 21 (represented by diamonds) was more increased than that of chromosome 1, but the overall variations are too high to discriminate the signals.

In addition, when the signal intensity ratio from each peak was analyzed (FIG. 7), the ratio value fluctuated above or below 0.5, and thus it is difficult to discriminate between amplification and reduction of signals. Specifically, the normal chromosome 1 has the ratio value of heterozygote near 0.5, and chromosome 21 (3n) has the ratio value near 0.66 and 0.33. Thus, it is difficult to discriminate between amplification and reduction of chromosome 21 of the sample (FIG. 7). Moreover, if the chromosome multiplication is higher than 8n (not 3n), or a small portion of chromosome is multiplied, it is difficult to distinguish the signals from background. For example, if amplification of chromosome or gene is more than 4 or 5 times, the ratio value becomes close to 1 or 0, which makes the analysis difficult.

As compared to the known methods having the above problems, the analysis method of using the mixture of normal control group and test sample of the present invention is advantageous in that chromosome multiplication can be easily distinguished, higher multiplication than 3n can be accurately analyzed, and the amplification of a small portion of chromosome can be also effectively analyzed.

What is claimed is:

1. A method for measuring the copy number variations in a chromosome, gene or specific nucleotide sequence, comprising the steps of:
   (a) mixing a homozygous DNA with a test sample DNA in a ratio of 1:1;
   (b) analyzing the DNA mixture to measure SNP signal by means of SNP array; and
   (c) determining the copy number variations in a chromosome, gene, or specific nucleotide sequence by measuring a signal ratio (SR) of SNP alleles from DNA mixture, wherein if the SNP alleles of the homozygous DNA and the test sample DNA are alter homozygous alleles, the signal ratio from such SNP alleles having no copy number variation is 1:1 and that having copy number variation is not 1:1, and wherein if the SNP allele of the test sample DNA is heterozygous allele, the signal ratio from such SNP alleles having no copy number variation is 1:3 or 3:1 and that having copy number variation is not 1:3 or 3:1.

2. The method according to claim 1, wherein the homozygous DNA is DNA of parthenogenetic or hydatidiform mole cell line.

3. The method according to claim 1, wherein the homozygous DNA is a cloned DNA fragment.

4. The method according to claim 1, wherein the SNP array is a SNP array designed to measure rare SNP.

* * * * *